United States Patent [19]
Kojima et al.

[11] 4,455,315
[45] Jun. 19, 1984

[54] N-(DIFLUOROMETHOXY SUBSTITUTED PHENYL)-DICHLOROMALEIMIDES USED IN AGRICULTURAL AND HORTICULTURAL FUNGICIDAL METHODS

[75] Inventors: Kazuhiro Kojima, Hiratsuka; Haruaki Ito, Kawasaki; Hiroshi Kubo, Yokohama, all of Japan

[73] Assignee: Showa Denko Kabushiki Kaisha, Tokyo, Japan

[21] Appl. No.: 318,982

[22] Filed: Nov. 6, 1981

[30] Foreign Application Priority Data
Nov. 10, 1980 [JP] Japan ................ 55-156950

[51] Int. Cl.³ ............................................ C07D 43/36
[52] U.S. Cl. ............................ 424/274; 548/549
[58] Field of Search ........... 260/326.5 FM; 548/549; 424/274

[56] References Cited
FOREIGN PATENT DOCUMENTS
1533067 11/1978 United Kingdom .

OTHER PUBLICATIONS
Kawada et al., Chemical Abstracts, vol. 80, p. 71, 34380r.
Kawada et al., Chemical Abstracts vol. 88, p. 162, 1609j.
Aoki et al., Chemical Abstracts vol. 84, p. 172, 55310r.
Boetsch et al., Chemical Abstracts vol. 89, p. 577, 215219b.

*Primary Examiner*—Paul M. Coughlan, Jr.
*Assistant Examiner*—D. B. Springer
*Attorney, Agent, or Firm*—Armstrong, Nikaido, Marmelstein & Kubovcik

[57] ABSTRACT

A 2,3-dichloro-N-difluoromethoxyphenylmaleimide of the formula (I):

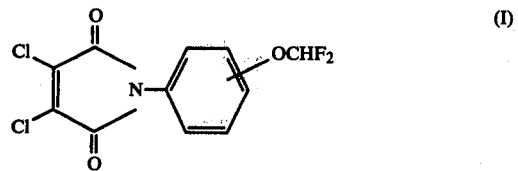

is useful as an agricultural and horticultural fungicide, particularly for fruit trees.

3 Claims, No Drawings

N-(DIFLUOROMETHOXY SUBSTITUTED PHENYL)-DICHLOROMALEIMIDES USED IN AGRICULTURAL AND HORTICULTURAL FUNGICIDAL METHODS

The present invention relates to a novel 2,3-dichloro-N-difluoromethoxyphenylmaleimide of the formula (I):

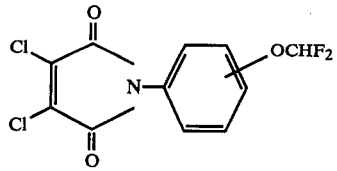

(I)

and an agricultural and horticultural fungicide comprising the compound as an active ingredient and a process for the preparation of the compound.

Some of N-phenylmaleimide derivatives are already known as fungicides. After it was discovered, in the 1940's by E. I. du Pont de Nemours & Co., Inc. in the United States of America, that N-phenylmaleimide has a fungicidal effect (see U.S. Pat. No. 2,444,536 issued on July 6, 1948), a large number of N-phenylmaleimide derivatives were synthesized and their physiological activities were examined and, as a result, some of them proved to exhibit some fungicidal effects. For example, Japanese Patent Publication No. 47-20012 discloses 2,3-dichloro-N-p-fluorophenylmaleimide (fluoroimide commercially available from Mitsubishi Chemical Industries Co., Ltd. under the trade name "Spatcide"); Japanese Patent Publication No. 47-223357 discloses compounds of the general formula (A); Japanese Patent Publication No. 47-43817 discloses compounds of the general formula (B); U.S. Pat. No. 3,890,270 discloses compounds of the general formula (C); Japanese Laid-open Application No. 50-129744 discloses compounds of the general formula (D); Japanese Laid-open Application No. 50-132129 discloses compounds of the general formula (E); German Offenlegungsschrift 2529359 discloses compounds of the general formula (F), and; German Offenlegungsschrift 2703266 discloses compounds of the general formula (G).

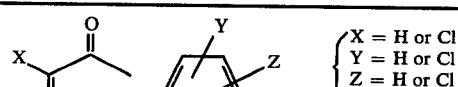

X = H or Cl
Y = H or Cl
Z = H or Cl (A)

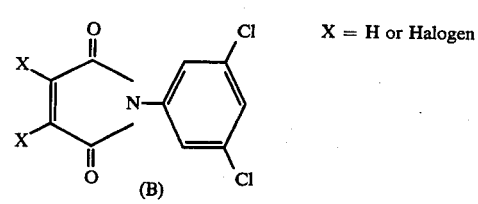

X = H or Halogen (B)

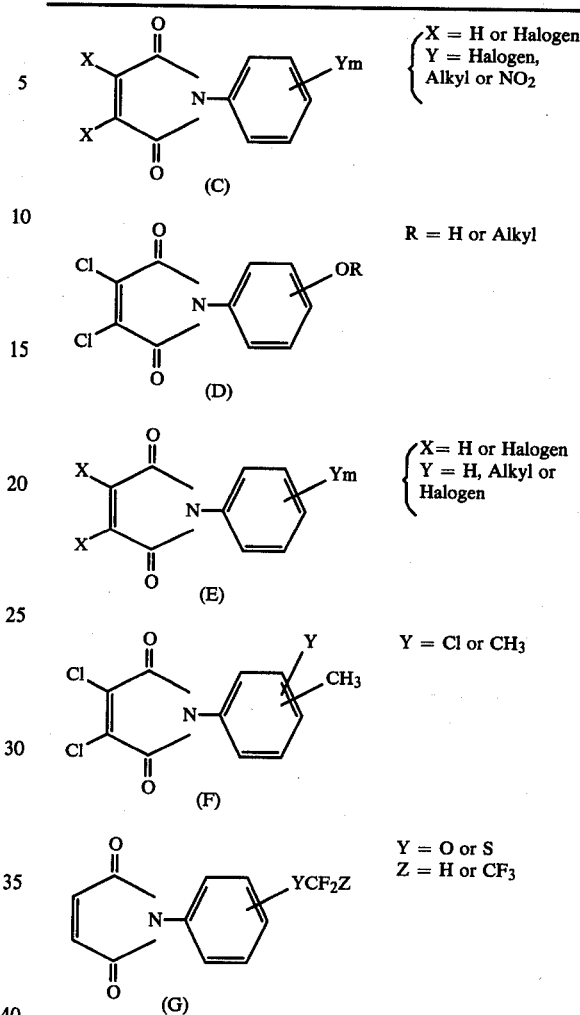

(C) X = H or Halogen; Y = Halogen, Alkyl or NO$_2$ (D) R = H or Alkyl (E) X = H or Halogen; Y = H, Alkyl or Halogen (F) Y = Cl or CH$_3$ (G) Y = O or S; Z = H or CF$_3$ These patented compounds are defective, however, in their practical use. The kinds of pathogens which can be controlled with these compounds, their fungicidal activities, their residual activities, their phytotoxicities and adherence to cultivated plants, toxicity to humans and animals, economical efficiency and the like had been heretofore checked and, as a result, most compounds were found not to be practically useful. The sole compound being put to the practical use at present is 2,3-dichloro-N-p-fluorophenylmaleimide (trade name: Spatcide) (from Mitsubishi Chemical Industries Co., Ltd.). This fungicide is, however, liable to cause leafburn to a wide variety of crops and trees. For example, this compound can not be applied to pear trees, strawberries, beans, and very many other crops owing to its severe phytotoxicity.

Accordingly, an object of the present invention is to provide compounds, practically useful as agricultural and horticultural fungicides, which do not have the above-mentioned problems caused by conventional N-phenylmaleimide derivatives and which have a low toxicity.

We have found that a 2,3-dichloro-N-difluoromethoxyphenylmaleimide of the above-mentioned formula (I) exhibits a broad spectrum of potent fungicidal effects, which can not be anticipated at all from the other known analogous compounds, as well as having a low toxicity.

The compounds according to the present invention exhibit an excellent effect in controlling damage to agricultural and horticultural crops caused by a wide variety of plant pathogens, and particularly, exhibit an excellent effect in practically controlling *Diaporthe citri, Elsinoe fawcetti, Glomerella ciugulata, Alternaria kikuchiana, Venturia nashicola, Venturia inaequalis, Alternaria mali, Sclerotinia mali, Marssonina mali, Cladosporium carpophilum, Cercospora kaki, Mycosphaerella nawae, Gloeosporium kaki, Mycosphaerella fijiensis, Glomerella cingulata, Alternaria solani, Peronospora destructor, Pseudoperonospora cubensis* and *Phytophthora infestans.*

The compound of the formula (I) according to the present invention can be prepared by a known method per se, for example, according to the following reaction scheme.

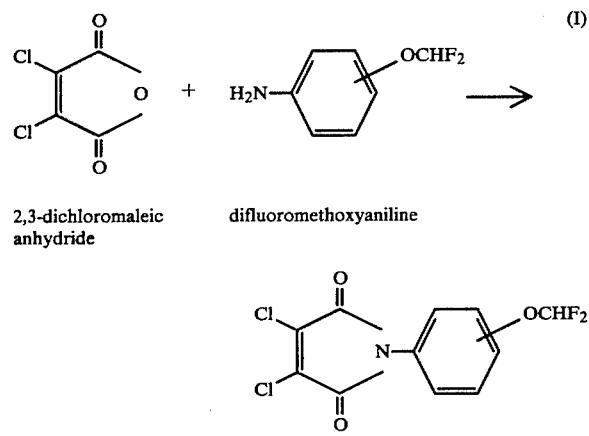

2,3-dichloromaleic anhydride    difluoromethoxyaniline

In case of carrying out the reaction shown by the above reaction scheme, a suitable solvent is desirably used.

The solvents used in the present invention include aromatic hydrocarbons such as benzene, toluene and xylene, chlorinated alkanes such as chloroform and carbon tetrachloride, ketones such as acetone and methylethylketone, lower alcohols such as methanol and ethanol, lower fatty acids such as acetic acid, dioxane and the like.

The difluoromethoxyaniline may be used in an amount equimolar with 2,3-dichloromaleic anhydride but, if necessary, may be increased or decreased to some extent.

The above-mentioned reaction may be effected, preferably at a temperature of between 40° and 120° C., normally for 1 to 3 hours. In case of using a water-soluble solvent, after the reaction is completed, the resulting reaction mixture is poured into water to crystallize the reaction product. Alternatively, in the case of using a water-insoluble solvent, after the reaction is completed, the solvent is removed, for example, by distilling it off under a reduced pressure to crystallize the reaction product. The resulting crude crystals are recrystallized from an organic solvent such as ethanol to give the desired compound in a good yield.

The compounds according to the present invention are novel and have not been described in any literature, patent specifications or the like. These compounds have such structural characteristics that the benzene ring of N-phenylmaleimide is substituted by a difluoromethoxy group and the 2- and 3-positions of the maleimide ring are substituted by a chlorine atom, respectively. As will be clear from the results of the below-mentioned tests, such structural characteristics of the compounds influence their physiological activities to a large extent, and especially, a compound having a difluoromethoxy group in the para-position of the benzene ring is markedly more effective than the other analogous compounds and causes substantially no phytotoxicity to crops. Further, in contrast with the above-mentioned known 2,3-dichloro-N-p-fluorophenylmaleimide, because the compounds according to the present invention have their fungicial activity which is not reduced by rain and cause no phytotoxicity to crops, they are more practically useful as fungicides. Furthermore, these compounds according to the present invention are considerably safe for humans and animals, for example, the peroral acute toxicity and ichthyotoxicity of 2,3-dichloro-N-p-difluoromethoxyphenylmaleimide is very low, the $LD_{50}$ for a four-week-old male mouse being more than 300 mg/Kg, and the Tlm48 for killifish being more than 10 ppm. According to a mutagenicity test (Ames test), both TA-100 and TA-98 are negative for 2,3-dichloro-N-p-difluoromethoxyphenylmaleimide.

As mentioned above, the compounds according to the present invention can be used, as agricultural and horticultural fungicides, as such or in admixture with a carrier (excipient) in the form of powders, granules, wettable powders, emulsions, emulsifiable concentrates or in any other suitable formulation form conventionally used for agricultural chemicals. In the latter case, if desired, the formulation may also contain a spreader, an emulsifier, a wetting agent, an adhesive and the like, and can be used in combination or admixture with other types of fungicides, pesticides, herbicides, fertilizers and the like.

The invention is now illustrated by, but by no means limited to, the following examples.

EXAMPLE 1

Preparation of 2,3-dichloro-N-(o-difluoromethoxyphenyl)maleimide 16.7 g (0.1 mole) of 2,3-dichloromaleic anhydride is dissolved in 100 ml of dioxane, and a solution of 15.9 g (0.1 mole) of o-difluoromethoxyaniline in 30 ml of dioxane is added dropwise to it at room temperature over 20 minutes with stirring. Thereafter, the resulting solution is stirred at 70°–80° C. for 2 hours and the dioxane is then distilled off under a reduced pressure. Water is added to the residue to precipitate crystals. The precipitated crystals are filtered off and recrystallized from ethanol to give 27.7 g (yield: 90%) of 2,3-dichloro-N-(o-difluoromethoxyphenyl)maleimide melting at 103.5°–104° C. in the form of light yellow crystals.

EXAMPLE 2

Preparation of 2,3-dichloro-N-(m-difluoromethoxyphenyl)maleimide 16.7 g (0.1 mole) of 2,3-dichloromaleic anhydride is dissolved in 100 ml of dioxane, and a solution of 15.9 g (0.1 mole) of m-difluoromethoxyaniline in 30 ml of dioxane is added dropwise to it at room temperature over 20 minutes with stirring. Thereafter, the resulting solution is stirred at 70°–80° C. for 2 hours and the dioxane is then distilled off under a reduced pressure. Water is added to the residue to precipitate crystals. The precipitated crystals are filtered off and recrystallized to give 29.2 g (yield: 95%) of 2,3-dichloro-N-(m-difluoromethoxyphenyl)maleimide melting at 122°–124° C. in the form of light yellow plate crystals.

EXAMPLE 3

Preparation of 2,3-dichloro-N-(p-difluoromethoxyphenyl)maleimide

A solution of 16.7 g (0.1 mole) of 2,3-dichloromaleic anhydride in 70 ml of toluene is heated to boiling. A solution of 15.9 g (0.1 mole) of p-difluoromethoxyaniline in 30 ml of toluene is added dropwise to it over 20 minutes with stirring. Thereafter, the resulting solution is refluxed until water is no longer distilled. This requires about 2 hours. The mixture is cooled to room temperature to precipitate crystals. The precipitated crystals are filtered off and washed with hexane to obtain 29.2 g of 2,3-dichloro-N-(p-difluoromethoxyphenyl)maleimide melting at 217.5°–218° C. in the form of light yellow plate crystals.

The physical data of the three compounds of the present invention prepared by the above Examples 1 through 3 are shown in the following Table 1. In the Table, the numerical values of the melting points were not corrected; the numerical values of NMR spectrum data were determined at 60 MHz using tetramethylsilane in deuterochloroform ($CDCl_3$) and deuterodimethylsulfoxide (DMSO), the symbols s, d, t, q and m representing peak patterns of singlet, doublet, triplet, quartet and multiplet, respectively and the symbol J representing a coupling constant, and; the shown numerical values of mass spectrum data are only the main peaks.

EXAMPLE 4

| Powders | |
|---|---|
| Compound of Example 3 | 3 parts by weight |
| Clay | 40 parts by weight |
| Talc | 57 parts by weight |

EXAMPLE 5

| Wettable Powders | |
|---|---|
| Compound of Example 3 | 75 parts by weight |
| Polyoxyethylenealkylarylether | 9 parts by weight |
| White carbon | 16 parts by weight |

Then, the physiological activity of the three compounds is examined by some typical testing methods and the obtained test results are shown in the following Examples 6 through 16. In carrying out these testing methods, for the purpose of comparison, some commercially available fungicides and some compounds, which are synthesized and are selected from the prior patents mentioned hereinbefore in view of being analogous to the compounds according to the present invention in chemical structures, are also tested and the obtained test results are also shown in the following Examples.

The compounds used for the tests in the following Examples are listed below.

TABLE 2

| Compound No. or Trade Name | Chemical Structure or Chemical Name |
|---|---|
| Compound of Present Invention | |
| 1 | ![structure] 2,3-dichloro-N-(o-difluoromethoxyphenyl)maleimide structure |
| 2 | 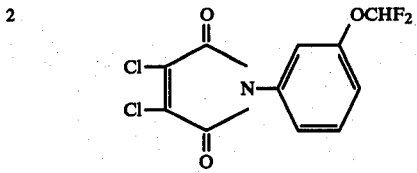 |

TABLE 1

| Example No. | Compound | Melting Point (°C.) | NMR (ppm)/Solvent | Mass Spectrum (m/e) |
|---|---|---|---|---|
| 1 | [structure with OCHF$_2$ ortho] | 103.5–104° C. | 6.45 (1H,t,J = 74) 7.06–7.58 (4H,m)/CDCl$_3$ | (M$^+$) 307, 257, 222, |
| 2 | [structure with OCHF$_2$ meta] | 122–124° C. | 7.27 (1H,t,J = 74) 7.10–7.80 (4H,m)/DMSO-d$_6$ | (M$^+$) 307, 257, 228, |
| 3 | [structure with OCHF$_2$ para] | 217.5–218° C. | 7.29 (1H,t,J = 74) 7.10–7.62 (4H,m)/DMSO-d$_6$ | (M$^+$) 307, 257, 228, |

TABLE 2-continued

| Compound No. or Trade Name | Chemical Structure or Chemical Name |
|---|---|
| 3 | 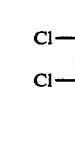 |
| Reference Compound | |
| 4 |  |
| 5 |  |
| 6 | 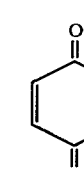 |
| 7 | 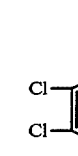 |
| 8 | 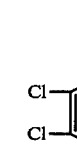 |
| 9 | 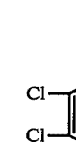 |
| Commercially Available Reference Compound | |
| iprodione | 1-Isopropylcarbamoyl-3-(3',5'-dichlorophenyl)-hydantoin |
| mancozeb | Zn—Mn—Ethylenebisdithiocarbamate |
| oxinecopper | 8-Hydroxyquinoline-Cu |
| fluoroimide | N—(p-Fluorophenyl)-2,3-dichloromaleimide |
| benomyl | Methyl-1-(butylcarbamoyl)-2-benzimidazolecarbamate |

EXAMPLE 6

Spore-germination Inhibiting Test for *Alternaria kukuchiana*

An apricot medium is inoculated with *Alternaria kikuchiana* and incubated at a temperature of 27° C. for 7–10 days to form conidia on the medium. The formed conidia are suspended in sterilized water and a diluted solution of each of the compounds according to the present invention (compound Nos. 1 through 3) in sterilized water is mixed with the resulting suspension of conidia to give a spore suspension containing twenty spores per microscopic field (magnification: X100) and the compound in a concentration of 10 ppm.

0.02 Ml of the prepared spore suspension containing the compound according to the present invention is dropped on a slide glass and incubated at a temperature of 27° C. under moist conditions for 20 hours. Thereafter, whether or not the spores germinate is examined under a microscope and the spore-germination rate is then calculated. For each compound, the above test is carried out in duplicate and the above microscopic examination is carried out on 200 spores.

For comparison, the above test is also carried out using six reference compounds (compound Nos. 4 through 9) and plain water.

The test results are shown in the following Table 3.

TABLE 3

| Compound No. | Spore-germination Rate (%) |
|---|---|
| 1 | 7 |
| 2 | 0 |
| 3 | 0 |
| 4 | 7 |
| 5 | 5 |
| 6 | 4 |
| 7 | 75 |
| 8 | 25 |
| 9 | 9 |
| — | 98 |

EXAMPLE 7

Pear Black Spot (*Alternaria kikuchiana*)-controlling Test

The wettable powders of each of the compounds according to the present invention (compound Nos. 1 through 3) are diluted with water to give a solution of the compound having a concentration of 500 ppm. The resulting solution is sprayed on unfolded leaves of potted young pears (variety: Nijū-seiki) in an amount corresponding to 600 1/10a per pot. After air-drying, the unfolded leaves are inoculated with *Alternaria kikuchiana*, by spraying a suspension of conidia thereof containing 30 conidia per microscopic field (magnification: X200). The suspension is prepared as described in the above Example 6.

After inoculation, the potted young pears are allowed to stand at a temperature of 27° C. in a moist room for one day and then transferred to a greenhouse. Six days after inoculation, the leaf area infested by pear black spot, i.e., the area of pathologic spots on a leaf is examined on 5 unfolded leaves per pot and an average infestation rate is then calculated.

For comparison, the above test is also carried out using seven reference compounds (compound Nos. 4 through 9 and iprodione) and plain water.

The test results are shown in the following Table 4.

TABLE 4

| Compound No. or Compound Name | Average Infestation Rate (%) (Based on infested area) | Phytotoxicity* of Treating Compound |
| --- | --- | --- |
| 1 | 9 | ± |
| 2 | 9 | ± |
| 3 | 2 | − |
| 4 | 15 | ± |
| 5 | 55 | +++ |
| 6 | 36 | ++ |
| 7 | 32 | ++ |
| 8 | 20 | ± |
| 9 | 28 | ± |
| iprodione | 11 | − |
| — | 80 | − |

*The phytotoxicity of the treating compound is evaluated according to the following criteria.

| | Damaged Area on Leaves |
| --- | --- |
| − | 0% |
| ± | 1-5% |
| + | 6-25% |
| ++ | 26-50% |
| +++ | ≧51% |

EXAMPLE 8

Citrus Melanose (*Diaporthe citri*)-controlling Test

The wettable powders of each of the compounds according to the present invention (compound Nos. 1 through 3) are diluted with water to give a solution of the compound having a concentration of 500 ppm. The resulting solution is sprayed, in an amount corresponding to 600 l/10a per pot, on potted young oranges (variety: Unshū) immediately after fresh leaves are unfolded. After one day, the potted young oranges are inoculated with *Diaporthe citri*, by spraying a suspension of spores thereof containing 50 spores per microscopic field (magnification: X200). The suspension is prepared by culturing *Diaporthe citri* on a dead branch of the above orange at a temperature of 25° C. for 60 days to form conidia and suspending the formed conidia in sterilized water to give a suspension of spores.

After inoculation, the potted young oranges are allowed to stand at a temperature of 25° C. in a moist room for two days and then transferred to a greenhouse. Twenty-four days after inoculation, the leaf area infested by citrus melanose, i.e., area of pathologic spots on a leaf is examined and the numbers of leaves infested by the disease are counted. Then, an infestation rate is calculated according to the following equation:

$$\text{Infestation Rate} = (\Sigma nf/4N) \times 100$$

wherein n is the number of leaves infested by disease, f is an infestation index and N is the total number of the examined leaves. The infestation index is as follows.

| Infestation Index | Infested Area on Leaf |
| --- | --- |
| 0 | 0-25% |
| 1 | 26-50% |
| 2 | 51-75% |
| 3 | 76-90% |
| 4 | 91-100% |

For comparison, the above test is also carried out using seven reference compounds (compound Nos. 4 through 9 and mancozeb) and plain water.

The test results are shown in the following Table 5.

TABLE 5

| Compound No. or Compound Name | Total Number of Examined Leaves | Number of Leaves Showing East Infestation Index | | | | | Infested Leaves (%) | Infestation Rate | Phytotoxicity* of Treating Compound |
| --- | --- | --- | --- | --- | --- | --- | --- | --- | --- |
| | | 0 | 1 | 2 | 3 | 4 | | | |
| 1 | 222 | 221 | 1 | 0 | 0 | 0 | 0.5 | 0.1 | − |
| 2 | 211 | 210 | 1 | 0 | 0 | 0 | 0.5 | 0.1 | − |
| 3 | 271 | 271 | 0 | 0 | 0 | 0 | 0 | 0 | − |
| 4 | 220 | 218 | 2 | 0 | 0 | 0 | 1.0 | 0.2 | − |
| 5 | 215 | 33 | 63 | 71 | 30 | 18 | 85 | 43 | ++ |
| 6 | 261 | 257 | 110 | 103 | 44 | 0 | 98 | 43 | + |
| 7 | 233 | 5 | 85 | 111 | 32 | 0 | 98 | 43 | + |
| 8 | 231 | 109 | 14 | 7 | 1 | 0 | 10 | 3.3 | − |
| 9 | 236 | 5 | 86 | 115 | 30 | 0 | 98 | 43 | − |
| mancozeb | 204 | 204 | 0 | 0 | 0 | 0 | 0 | 0 | − |
| — | 213 | 2 | 28 | 61 | 71 | 51 | 99 | 67 | − |

*This is evaluated according to the same criteria as described in the above Example 7.

EXAMPLE 9

Test of Residual Activity against Citrus Melanose (*Diaporthe citri*)

Each of the compounds of the present invention (compound Nos. 1 through 3) is diluted with water to give a solution having a concentration of 1000 ppm. The resulting solution is sprayed, in an amount corresponding to 600 l/10a per pot, on potted young oranges (variety: Unshū) immediately after fresh leaves are unfolded. After air-drying, the potted young oranges are exposed to 23 mm/hr of rain.

One day after the spray treatment, the unfolded leaves are inoculated with *Diaporthe citri*, by spraying a suspension of spores thereof containing 50 spores per microscopic field (magnification: X200). The suspension is prepared as described in the above Example 8.

After inoculation, the potted young oranges are allowed to stand at a temperature of 25° C. in a moist room for two days and then transferred to a greenhouse. Twenty-four days after inoculation, examination is carried out in the manner as described in the above Example 8.

For comparison, the above test is also carried out using eight reference compounds (compound Nos. 4 through 9 and oxinecopper and mancozeb) and plain water.

The test results are shown in the following Table 6.

TABLE 6

| Compound No. or Compound Name | Total Number of Examined Leaves | Number of Leaves Showing Each Infestation Index | | | | | Infested Leaves (%) | Infestation Rate | Phytotoxicity* of Treating Compound |
| --- | --- | --- | --- | --- | --- | --- | --- | --- | --- |
| | | 0 | 1 | 2 | 3 | 4 | | | |
| 1 | 156 | 122 | 27 | 6 | 1 | 0 | 22 | 7 | ± |
| 2 | 185 | 181 | 4 | 0 | 0 | 0 | 2 | 0.5 | ± |
| 3 | 187 | 187 | 0 | 0 | 0 | 0 | 0 | 0 | − |
| 4 | 165 | 30 | 82 | 43 | 10 | 0 | 82 | 30 | + |
| 5 | 172 | 22 | 43 | 72 | 28 | 7 | 87 | 43 | ++ |
| 6 | 159 | 15 | 86 | 45 | 13 | 0 | 91 | 34 | + |
| 7 | 163 | 115 | 36 | 11 | 1 | 0 | 29 | 9 | + |
| 8 | 161 | 35 | 58 | 61 | 7 | 0 | 78 | 31 | − |
| 9 | 177 | 113 | 45 | 18 | 1 | 0 | 36 | 12 | − |
| oxinecopper | 187 | 35 | 113 | 37 | 2 | 0 | 81 | 26 | ± |
| mancozeb | 159 | 159 | 0 | 0 | 0 | 0 | 0 | 0 | − |
| — | 184 | 0 | 3 | 67 | 84 | 30 | 100 | 69 | − |

*This is evaluated according to the same criteria as described in the above Example 7.

EXAMPLE 10

Apple Alternaria Leaf Spot (*Alternaria mali*)-controlling Test

The compound according to the present invention (compound No. 3) is diluted with water to give a solution having a concentration of 500 ppm. The resulting solution is sprayed, in an amount corresponding to 600 l/10a per pot, on fresh twigs of potted apples (variety: Star King) immediately after fresh leaves are unfolded.

After one day, the twigs are inoculated with *Alternaria mali*, by spraying a suspension of spores thereof containing 50 spores per microscopic field (magnification: X200). The suspension is prepared by culturing *Alternaria mali* on an apricot medium at a temperature of 28° C. for 9 days to form conidia and suspending the formed conidia in sterilized water to give a suspension of spores.

After inoculation, the potted apples are allowed to stand at a temperature of 27° C. in a moist room for one day and then transferred to a greenhouse. Six days after inoculation, the leaf area infested by Alternaria leaf spot, i.e., area of pathologic spots on a leaf is examined on 5 unfolded leaves per pot and an average infestation rate is then calculated.

For comparison, the above test is also carried out using plain water.

The test results are shown in the following Table 7.

TABLE 7

| Compound No. | Average Infestation Rate (%) (Based on infested area) |
| --- | --- |
| 3 | 0 |
| — | 90 |

EXAMPLE 11

Cucumber Downy Mildew (*Pseudoperonospora cubensis*)-controlling Test

The compound according to the present invention (compound No. 3) is diluted with water to give a solution having a concentration of 1000 ppm. The resulting solution is sprayed on leaves of cucumbers at second true leaves stage, which have been cultivated in unglazed pots having a diameter of 10 cm, in an amount of 60 ml per pot. After one day, the cucumbers are inoculated with *Pseudoperonospora cubensis*, by spraying a suspension thereof containing 30 spores per microscopic field (magnification: X200), which are collected from the leaves infested by cucumber downy mildew.

After inoculation, the potted cucumbers are allowed to stand at a temperature of 20° C. in a moist room for one day and then transferred to a greenhouse. Five days after inoculation, the leaf area infested by cucumber downy mildew is examined. In this test, one cucumber is planted in each pot and three pots are used.

For comparison, the above test is also carried out using plain water.

The test results are shown in the following Table 8.

TABLE 8

| Compound No. | Average Infestation Rate (%) (Based on infested area) |
| --- | --- |
| 3 | 0 |
| — | 100 |

EXAMPLE 12

Citrus Scab (*Elsinoe fawcetti*)-controlling Test

The wettable powders of the compound according to the present invention (compound No. 3) are diluted with water to give a solution of the compound having a concentration of 250 ppm. The resulting solution is sprayed, in an amount corresponding to 600 l/10a per pot, on potted young oranges (variety: Unshū) immediately after fresh leaves are unfolded. After one day, the potted young oranges are inoculated with *Elsinoe fawcetti*, by spraying a suspension of crushed hyphae thereof containing 50 crushed hyphae per microscopic field (magnification: X100). The suspension is prepared by culturing *Elsinoe fawcetti* on potato medium at a temperature of 25° C. for 30 days to form hyphae and suspending it in sterilized water.

After inoculation, the potted young oranges are allowed to stand at a temperature of 25° C. in a moist room for two days and then transferred to a greenhouse. Twenty-three days after inoculation, the leaf infested by citrus scab is examined, i.e., number of pathologic spots on a leaf is examined and the numbers of leaves infested by cirtrus scab are counted. Then, an infestation rate is calculated according to the following equation:

$$\text{Infestation Rate} = (\Sigma nf/3N) \times 100$$

wherein n is the number of the infested leaves, f is an infestation index and N is the total number of the examined leaves. The infestation index is as follows.

| Infestation Index | Number of Pathologic Spots per Leaf |
| --- | --- |
| 0 | 0 |
| 1 | 1–3 |
| 2 | 4–10 |
| 3 | ≧11 |

For comparison, the above test is also carried out using a reference compound (benomyl) and plain water.
The test results are shown in the following Table 9.

TABLE 9

| Compound No. or Compound Name | Total Number of Examined Leaves | Number of Leaves Showing Each Infestation Index | | | | Infested Leaves (%) | Infestation Rate | Phytotoxicity* of Treating Compound |
| --- | --- | --- | --- | --- | --- | --- | --- | --- |
| | | 0 | 1 | 2 | 3 | | | |
| 3 | 313 | 311 | 2 | 0 | 0 | 0.6 | 0.2 | — |
| benamyl | 330 | 328 | 2 | 0 | 0 | 0.6 | 0.2 | — |
| — | 268 | 65 | 123 | 59 | 21 | 76 | 38 | — |

*This is evaluated according to the same criteria as described in the above Example 7.

| Infestation Index | Infested Area on Leaf |
| --- | --- |
| 0 | 0% |
| 1 | 1–25% |
| 2 | 26–50% |
| 3 | 51–100% |

For comparison, the above test is also carried out using a reference compound (mancozeb) and plain water.
The test results are shown in the following Table 10.

TABLE 10

| Compound No. or Compound Name | Total Number of Examined Leaves | Number of Leaves Showing Each Infestation Index | | | | Infested Leaves (%) | Infestation Rate | Phytotoxicity* of Treating Compound |
| --- | --- | --- | --- | --- | --- | --- | --- | --- |
| | | 0 | 1 | 2 | 3 | | | |
| 3 | 20 | 20 | 0 | 0 | 0 | 0 | 0 | — |
| mancozeb | 20 | 20 | 0 | 0 | 0 | 0 | 0 | — |
| — | 20 | 0 | 10 | 9 | 1 | 100 | 51.7 | — |

*This is evaluated according to the same criteria as described in the above Example 7.

EXAMPLE 13

Potato Late Blight (*Phytophthora infestans*)-controlling Test

The wettable powders of the compound according to the present invention (compound No. 3) are diluted with water to give a solution of the compound having a concentration of 500 ppm. The resulting solution is sprayed, in an amount corresponding to 600 l/10a per pot, on potted potatoes (variety: Chippewa) immediately after fresh leaves are unfolded. After one day, the potted potatoes are inoculated with *Phytophthora infestans*, by spraying a suspension of zoospores thereof containing 50 zoospores per microscopic field (magnification: X200). The suspension is prepared by culturing *Phytophthora infestans* on potatoes at a temperature of 21° C. for 7 days to form zoospores and suspending the formed zoosperes in sterilized water to give a suspension of zoospores.

After inoculation, the potted potatoes are allowed to stand at a temperature of 20° C. in a moist room for one day and then transferred to a greenhouse. Six days after inoculation, the leaf area infested by potato late blight, i.e., the area of pathologic spots on a leaf is examined on four leaves per pot and an infestation rate is then calculated according to the following equation:

Infestation Rate = $(\Sigma nf/3N) \times 100$ wherein n is the number of the infested leaves, f is an infestation index and N is the total number of the examined leaves. The infestation index is as follows.

EXAMPLE 14

Apple Scab (*Venturia inaequalis*)-controlling Test

The compound according to the present invention (compound No. 3) is diluted with water to give a solution having a solution of 500 ppm. The resulting solution is sprayed, in an amount corresponding to 600 l/10a per pot, on fresh twigs of potted apples (variety: Star King) immediately after fresh leaves are unfolded.

One day after the spray treatment, the twigs are inoculated with *Venturia inaequalis*, by spraying a suspension of spores thereof containing 50 spores per microscopic field (magnification: X200). The suspension is prepared by culturing *Venturia inaequalis* on an apricot medium at a temperature of 23° C. for 7 days to form conidia and suspending the formed conidia in sterilized water to give a suspension of spores.

After inoculation, the potted apples are allowed to stand at a temperature of 23°–25° C. in a moist room for one day and then transferred to a greenhouse. Seven days after inoculation, the leaf area infested by apple scab, i.e., the area of pathologic spots on a leaf is examined on 5 unfolded leaves per pot and an infestation rate is then calculated according to the following equation:

Infestation Rate = $(\Sigma nf/3N) \times 100$ wherein n is the number of the infested leaves, f is an infestation index and N is the total number of the examined leaves. The infestation index is as follows.

| Infestation Index | Infested Area on Leaf |
| --- | --- |
| 0 | 0% |
| 1 | 1–25% |

-continued

| Infestation Index | Infested Area on Leaf |
|---|---|
| 2 | 26–50% |
| 3 | 51–100% |

For comparison, the above test is also carried out using a reference compound (benomyl) and plain water.

The test results are shown in the following Table 11.

TABLE 11

| Compound No. or Compound Name | Total Number of Examined Leaves | Number of Leaves Showing Each Infestation Index | | | | Infested Leaves (%) | Infestation Rate | Phytotoxicity* of Treating Compound |
|---|---|---|---|---|---|---|---|---|
| | | 0 | 1 | 2 | 3 | | | |
| 3 | 25 | 25 | 0 | 0 | 0 | 0 | 0 | — |
| benamyl | 25 | 25 | 0 | 0 | 0 | 0 | 0 | — |
| — | 25 | 0 | 8 | 15 | 2 | 100 | 58.7 | — |

*This is evaluated according to the same criteria as described in the above Example 7.

EXAMPLE 15

Test of Phytotoxicity to Pears

The wettable powders of the compound according to the present invention (compound No. 3) are diluted with water to a given concentration. The resulting solution of wettable powders is sprayed, in an amount corresponding to 600 l/10a per pot, on potted pears (variety: Nijū-seiki) immediately after fresh leaves are unfolded. After air-drying, the potted pears are allowed to stand in a greenhouse. Two weeks after the spray treatment, the phytotoxicity of the compound according to the present invention, to the potted pears is carefully examined.

For comparison, the above test is also carried out using a reference compound (fluoroimid) and plain water.

The test results are shown in the following Table 12.

TABLE 12

| Compound No. or Compound Name | Formulation Form | Dilution | Sprayed Amount | Phytotoxicity* of Treating Compound |
|---|---|---|---|---|
| 3 | 75% Wettable Powders | × 750 | 600 l/10 a | — |
| 3 | 75% Wettable Powders | × 500 | 600 l/10 a | — |
| fluoroimide | 75% Wettable Powders | × 750 | 600 l/10 a | + |
| fluoroimide | 75% Wettable Powders | × 500 | 600 l/10 a | ++ |
| — | — | — | — | — |

*This is evaluated according to the same criteria as described in the above Example 7.

EXAMPLE 16

Test of Phytotoxicity to Apples

The wettable powders of the compound according to the present invention (compound No. 3) are diluted with water to a given concentration. The resulting solution of wettable powders is sprayed, in an amount corresponding to 600 l/10a per pot, on potted apples (variety: Star King) immediately after fresh leaves are unfolded. After air-drying, the potted apples are allowed to stand in a greenhouse. Two weeks after the spray treatment, the phytotoxicity, of the compound according to the present invention, to the potted apples is examined.

For comparison, the above test is also carried out using a reference compound (fluoroimide) and plain water.

The test results are shown in the following Table 13.

TABLE 13

| Compound No. or Compound Name | Formulation Form | Dilution | Sprayed Amount | Phytotoxicity* of Treating Compound |
|---|---|---|---|---|
| 3 | 75% Wettable Powders | × 750 | 600 l/10 a | — |
| fluoroimide | 75% Wettable Powders | × 750 | 600 l/10 a | + |
| — | — | — | — | — |

*This is evaluated according to the same criteria as described in the above Example 7.

We claim:

1. A method for controlling damage to agricultural and horticultural crops caused by plant pathogens, which comprises:
applying an effective amount of an agricultural and horticultural fungicide which comprises a 2,3-dichloro-N-difluoromethoxyphenylmaleimide of the formula (I):

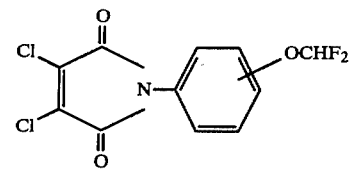

(I)

as an active ingredient.

2. A method for controlling damage to agricultural and horticultural crops caused by plant pathogens, as claimed in claim 1, wherein said crops are fruit trees.

3. A method for controlling damage to agricultural and horticultural crops caused by plant pathogens, as claimed in claim 1, wherein said active ingredient is 2,3-dichloro-N-(p-difluoromethoxyphenyl)maleimide.

* * * * *